Figure 1:
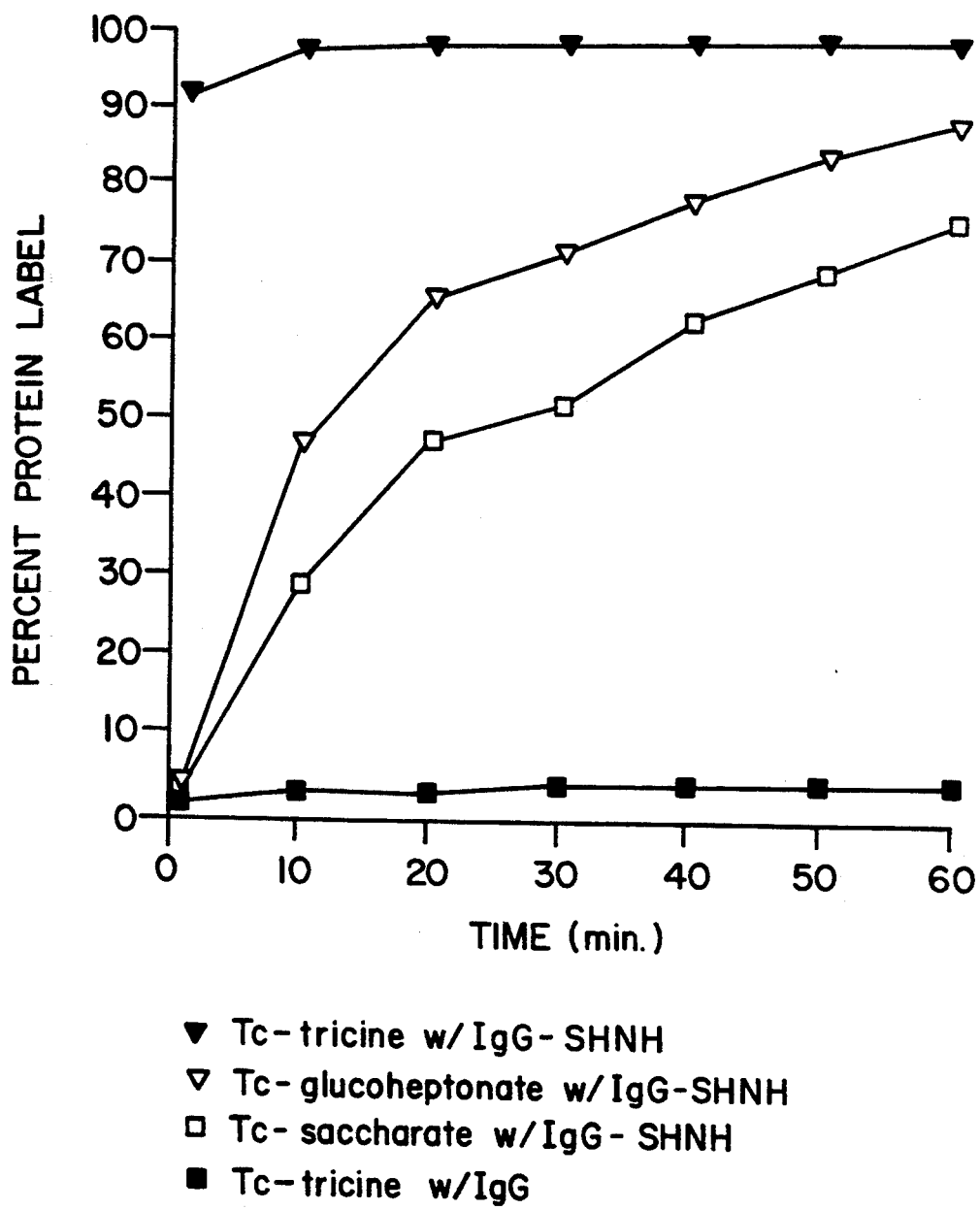

United States Patent [19]

Bridger et al.

[11] Patent Number: 5,350,837
[45] Date of Patent: Sep. 27, 1994

[54] COMPLEXES WITH $^{99m}$TC SUITABLE FOR RADIOLABELLING MONOCLONAL ANTIBODIES OR OTHER MACRO MOLECULES

[75] Inventors: Gary J. Bridger, Bryn Mawr; Pedro E. Hernandez, Malvern; John D. Higgins, III; Scott K. Larsen, both of West Chester, all of Pa.

[73] Assignee: Johnson Matthey Public Limited Company, London, England

[21] Appl. No.: 55,312

[22] Filed: May 3, 1993

[30] Foreign Application Priority Data

May 2, 1992 [GB] United Kingdom ............ 92/09641.1

[51] Int. Cl.$^5$ ............................................ C07F 13/00
[52] U.S. Cl. .................................... 534/14; 530/391.5
[58] Field of Search .................. 534/14; 424/1.1, 1.65; 530/391.5

[56] References Cited

U.S. PATENT DOCUMENTS

| | | | |
|---|---|---|---|
| 4,017,596 | 4/1977 | Loberg et al. | 424/1.1 |
| 4,113,850 | 9/1978 | Benes | 424/1.1 |
| 4,425,280 | 1/1984 | Ito | 260/429.9 |
| 4,772,724 | 9/1988 | Wright et al. | 548/403 |
| 5,198,208 | 3/1993 | Berg et al. | 424/1.1 |

FOREIGN PATENT DOCUMENTS

0384769  8/1990  European Pat. Off. .

OTHER PUBLICATIONS

Mighri et al., Bulletin De La Societe Chimique De France, No. 5-6, 1975, pp. 1160-1654.
Chemical Abstracts, vol. 79, 1973, Abstract No. 66815g, Frezou et al., p. 485, J. Chim. Phys. Physicochim. Biol., vol. 70, No. 5, 1973, pp. 861-863.
Chemical Abstracts, vol. 89, 1978, Abstract No. 80938n, Kapoor et al., p. 360, J. Inorg. Nucl. Chem., vol. 40, No. 1, 1978, pp. 155-158.
Chemical Abstracts, vol. 95, 1981, Abstract No. 9305u, Kalincak et al., p. 253, Int. J. Appl. Radiat. Isot., vol. 32, No. 7, 1981, pp. 493-499.
Kishan, et al., "Complex Formation of Indium(III) with N-[tris(hydroxy-methyl)methyl]glycine and N,N-(-dihydroxymethyl)glycine", *Trans. Saest* 15(4), 327-31, 1980; published in *Chem. Abs.* as CA95(2): 13633r, Jul. 6, 1981.

*Primary Examiner*—Robert L. Stoll
*Assistant Examiner*—Lara E. Chapman
*Attorney, Agent, or Firm*—Cushman Darby & Cushman

[57] ABSTRACT

The ligand L, $(R^3)(R^4)(R^5)C-N(R)-C(R^1)(R^2)-(CH_2)_n-COOH$ L where R is hydrogen, hydroxy, alkyl, hydroxyalkyl, or alkylcarboxy, or R and $R^1$ together may form a mono-, di-, tri-, or tetra-methylene radical, or R and $R^3$ together may form a mono-, di-, tri-, or tetra-methylene radical, and $R^1$ and $R_2$ may be the same or different and are selected from hydrogen, hydroxy, alkyl, hydroxyalkyl, carboxy, alkylcarboxy, alkylamine, alkylthiol, aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy, alkylcarboxy, provided that at least one of $R^3$, $R^4$ and $R^5$ is hydroxyalkyl, and n is equal to 0, 1 or 2, for example tricine, form useful complexes with $^{99m}$Tc, for radiolabelling macromolecules such as monoclonal antibodies.

9 Claims, 3 Drawing Sheets

COMPLEXES WITH $^{99m}$TC SUITABLE FOR RADIOLABELLING MONOCLONAL ANTIBODIES OR OTHER MACRO MOLECULES

The present invention concerns improvements in radiolabelling, and more especially it concerns improved radioisotope complexes.

Because of their high biological specificity, certain macromolecules such as monoclonal antibodies, have been used to target radioisotopes to specific in vivo sites for imaging for diagnostic purposes or for therapy. The use of the metastable isotope of technetium $^{99m}$Tc, in diagnostic nuclear medicine is welt established, and the beta-emitting isotopes of rhenium $^{186}$Re, $^{188}$Re and $^{189}$Re can be used therapeutically.

A number of methods for attaching technetium to macromolecules have been described in the scientific and patent literature. We refer to our EPA 0 384 769 which discusses this area, and teaches methods of modifying macromolecules to permit more ready linking to radioisotope complexes. For example, the method currently preferred in the art for preparing the radiolabelled macromolecule is to reduce the pertechnetate ion $Tc^{VII}O_4^-$ in the presence of a chelating precursor, to form a labile Tc-precursor complex which is then reacted with a metal binding group on a modified protein to form a Tc-protein conjugate. A number of chelating precursors of this type have been described for technetium which include sodium glucoheptonate, sodium tartrate, sodium gluconate, sodium saccharate and sodium 1,1,3,3-propylenetetraphosphonate.

The presently favoured chelating precursor is sodium glucoheptonate. Use of Tc-glucoheptonate to radiolabel a protein which has been functionally modified with hydrazino-nicotinamide (SHNH) groups as disclosed in the above-mentioned EPA 0384 769 requires an incubation of 60 minutes, and although radiolabelling yields >95% can be achieved, this is at a rather low specific activity of <10 mCi/mg protein. It is an aim of the present invention to improve upon the time required for incubation and/or the specific activity, by providing a novel Tc-complex.

The present invention provides a complex of technetium with the ligand L

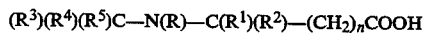   L where
R is hydrogen, hydroxy, alkyl, hydroxyalkyl, or alkylcarboxy, or R and $R^1$ together may form a mono-, di-, tri-, or tetra-methylene radical, or R and $R^2$ together may form a mono, di-, tri-, or tetra-methylene radical, and $R^1$ and $R^2$ may be the same or different and are selected from hydrogen, hydroxy, alkyl, hydroxyalkyl, carboxy, alkylcarboxy, alkylamine, alkylthiol, aryl or $R^1$ and $R^2$ together may form a tetra- or penta-methylene radical, and $R^3$ and $R^4$ and $R^5$ may be the same or different and are selected from hydrogen, hydroxy, alkyl, hydroxyalkyl, carboxy, alkylcarboxy, provided that at least one of $R^3$, $R^4$ and $R^5$ is hydroxyalkyl, and n is equal to 0, 1 or 2.

Preferred alkyl and substituted alkyl groups for R are alkyl of 1 to 3 carbon atoms. Preferably, when $R^1$ and $R^2$ are alkyl or substituted alkyl, they are 1 to 4 carbon atoms. Preferred aryl groups are phenyl and benzyl.

Preferably, when $R^3$ and $R^4$ and $R^5$ are alkyl or substituted alkyl groups they are of 1 to 3 carbon atoms.

Preferably, at least one of R, $R^1$ and $R^2$ is hydrogen and at least one of $R^3$, $R^4$ and $R^5$ is hydroxymethyl. A particularly preferred ligand is N-[tris(hydroxymethyl)-methyl]glycine, also known as tricine, which name will be used hereinafter. Other desirable ligands L are those in which R, $R^1$ and $R^2$ are all hydrogen, $R^3$ is hydrogen, methyl or ethyl, and $R^4$ and $R^5$ are hydroxymethyl or 2-hydroxyethyl; R, $R^1$ and $R^2$ are all hydrogen, $R^3$ and $R^4$ are hydrogen or methyl, and $R^5$ is hydroxymethyl or 2-hydroxethyl. Also desirable are ligands L in which R and $R^1$ are both hydrogen. $R^2$ is methyl hydroxy, hydroxymethyl, carboxy, carboxymethyl, 2-carboxyethyl, phenyl, benzyl, 1-hydroxyethyl or mercaptomethyl, and $R^3$, $R^4$ and $R^5$ are all hydroxymethyl; R is hydrogen, $R^1$ and $R^2$ are both methyl, and $R^3$, $R^4$ and $R^5$ are all hydroxymethyl; R is hydroxy, hydroxymethyl, or carboxymethyl, $R^1$ and $R^2$ are both hydrogen, and $R^3$, $R^4$ and $R^5$ are all hydroxymethyl.

The invention further provides a method for the formation of the complex of the invention, comprising reducing the pertechnetate ion in the presence of a ligand of general formula L.

The method of the invention is desirably carried out in aqueous solution, using stannous ion, for example as stannous chloride. It is possible that other reducing systems may be used, however, provided that there is no significant adverse effect upon the purity and stability of the product complex but stannous ion reduction is at present regarded as the best practicable method. The method proceeds well under generally known conditions and at room temperature.

The invention also provides labelled macromolecules produced from a modified macromolecule and the complex of the invention. It is possible that the ligand L remains as a co-ligand on the labelled macromolecule, but this has not yet been proved.

Certain of the ligands disclosed herein are novel, in particular N-[bis(hydroxymethyl)methyl]glycine, hereinafter also called dicine. It is believed that the class of ligands of general formula I

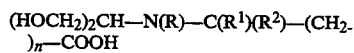   I in which R, $R^1$, $R^2$ and n are as defined above, are novel and therefore form part of the present invention.

The ligands of formula I may be prepared by methods generally available to the skilled synthetic chemist, suitably by reacting bis(hydroxymethyl)methylamine with a functionalised acid derivative of general formula II

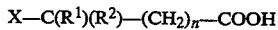   II in which $R^1$, $R^2$ and n are as defined above, and X is a reactive group, for example a halogen, methyl- or toluene-sulphonate or trifluoromethylsulphonate, in the presence of a base.

Figure 2:
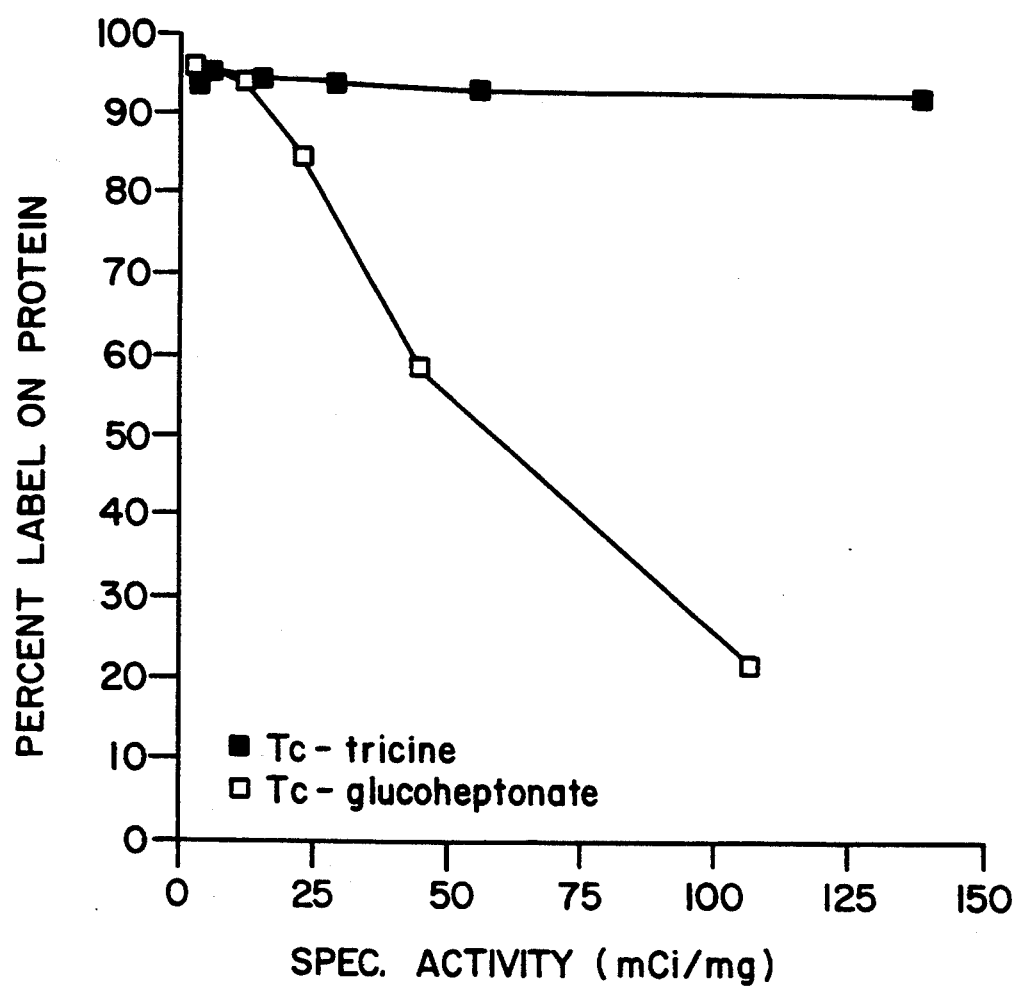
Figure 3:
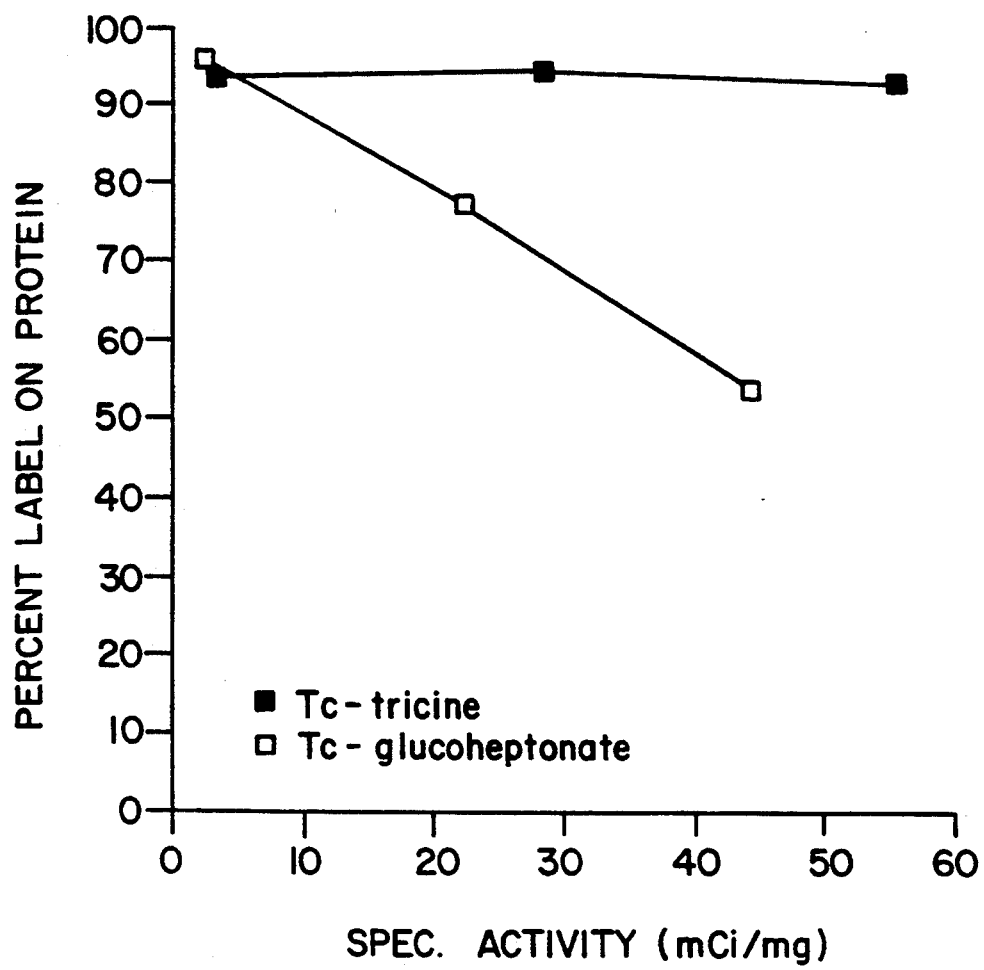

The invention is more particularly described in the Examples below and with reference to the accompanying Figures, of which FIG. 1 is a comparison of the rate of radiolabelling of IgG-SHNH with three different Tc-precursor complexes, at room temperature, FIG. 2 is a comparison of radiolabelling of IgG by two Tc-precursor complexes at varying levels of specific activity, and FIG. 3 is a comparison of radiolabelling serial dilutions of IgG with two Tc-precursor complexes as a function of specific activity.

The description of the invention below is to be regarded as illustrative and in no way limiting of the invention.

EXAMPLE 1 a) Preparation of a Tricine/SnCl$_2$ Lyophilized Kit 98 ml of chromatography grade (glass distilled and filtered) water which had been deoxygenated by boiling and cooling under argon was measured into an acid washed, rinsed and dried 150 ml Edenmeyer flask containing 3.60 g of N-[tris(hydroxymethyl)methyl]glycine (tricine). The pH of the solution was adjusted to 7.1 using approximately 2.3 ml of 1N NaOH solution. The flask was sealed with an airtight septa and purged an additional 60 minutes with argon by canula. A solution of SnCl$_2$—2H$_2$O, 50 mg/ml in deoxygenated 0.1N HCl, was prepared under argon and 80 uL added to the tricine solution. One milliliter of the tricine/SnCl$_2$ solution was transferred by syringe to an argon filled, septa-capped vial, frozen, and subsequently lyophillized. The lyophillized vials were capped and crimped under argon to render a final composition of 36 mg tricine and 0.04 mg SnCl$_2$ at pH 7.1.

b) Reconstitution of a Tricine/SnCl$_2$ Lyophillized Kit Formation of $^{99m}$Tc-tricine A septa-capped vial of lyophillized tricine/SnCl$_2$ composition is injected with 1 ml of $^{99m}$TcO$_4^-$ (20 mCi/ml) and immediately upon injection shaken vigorously until all the freeze-dried material is dissolved. Upon dissolution the Tc-tricine sample is left for 15 to 30 minutes at room temperature before analysis. Analysis for formation of the Tc-tricine precursor complex is performed on ITLC-SG chromatography plates. Using an 8×1 cm plate, a 2.5 uL sample of the Tc-tricine solution is spotted at 1 cm and eluted with saline to yield <1% Tc-colloid at the origin and >99% Tc-tricine at the solvent front. Using a 10×1 cm plate, a 2.5 uL sample of Tc-tricine solution is spotted at 1 cm and eluted with a 2:1 acetone:dichloromethane solution to yield >99% $^{99m}$Tc-tricine at the origin and <1% TcO$_4^-$ at the solvent front.

Immunoglobulin (IgG) (MW=approximately 155,000) was conjugated with SHNH according to Example 9 of the EPA 0384 769, and was used in the tests described below.

EXAMPLE 2

The rate of radiolabelling IgG modified with SHNH was measured with respect to three Tc-precursor complexes:Tc-tricine, Tc-glucoheptonate, and Tc-saccharate. 100 uL of the respective Tc-precursor at 15 mCi/ml was mixed with an equal volume of IgG-SHNH at 4.9 mg/ml and incubated for one hour at room temperature. Each solution was sampled at 1, 10, 20, 30, 40, 50 and 60 minutes and analyzed by ITLC-SG chromatography using standard techniques. In addition, Tc-tricine was mixed with an equal volume of unmodified IgG to measure its non-specific radiolabelling to the protein. The results, presented in FIG. 1, clearly demonstrate that within minutes Tc-tricine radiolabels the protein greater than 90% whereas Tc-glucoheptonate requires one hour. Additionally, the extent of radiolabelling reaches a maximum within thirty minutes for Tc-tricine versus Tc-glucoheptonate which again requires one hour. Tc-saccharate is clearly the least effective radiolabelling precursor for IgG-SHNH. Tc-tricine, in the absence of hydrazino-nicotinamide linkers on the protein, only radiolabels unmodified IgG to a maximum of 4%. Therefore, the utilisation of tricine in the formation of the Tc-precursor complex dramatically improves the labelling of modified IgG over utilising glucoheptonate.

EXAMPLE 3

The percent yield of radiolabelling IgG modified with SHNH was measured as a function of the specific activity (mCi of $^{99m}$TC per mg of protein) of the solutions with respect to two Tc-precursors; Tc-glucoheptonate which was the better of the prior art precursors determined according to Example 2 above, and Tc-tricine. Two series of vials containing 100, 50, 20, 10, 5 and 2 uL of an IgG-SHNH solution (4.9 mg/ml in protein) were prepared. To each vial of one series was added 100 uL of the respective Tc-precursor and the vials incubated at 27° C. for one hour. The test solutions were analysed by ITLC-SG chromatography using standard techniques. The results, presented in FIG. 2, demonstrate >90% radiolabelling of the protein for specific activities of Tc-tricine as high as 140 mCi/mg versus Tc-glucoheptonate which shows a dramatic decrease in radiolabelling efficiency as the specific activity increases above 25 mCi/mg. Therefore, the utilisation of Tc-tricine improves upon the efficiency of radiolabelling low concentrations of protein.

EXAMPLE 4

The percent yield of radiolabelling IgG modified with SHNH was measured as a function of the specific activity (mCi of $^{99m}$Tc per mg of protein) for dilute solutions of protein with respect to two Tc-precursors: Tc-tricine and Tc-glucoheptonate. From a stock solution of IgG-SHNH, 4.9 mg/ml in citrate buffer pH 5.2, a solution of 10× dilution and a solution of 20× dilution with citrate buffer were prepared. A 100 uL sample of each protein solution (at 4.9, 0.49 and 0.25 mg IgG-SHNH/ml) was mixed with an equal volume of Tc-precursor solution and incubated for one hour at 37° C. The test solutions were analysed by ITLC/SG chromatography using standard techniques. The results, presented in FIG. 3, demonstrate that under buffered conditions, Tc-tricine continues to radiolabel modified protein in greater than 90% efficiency at higher specific activities than Tc-glucoheptonate.

EXAMPLE 5

Synthesis of N-[bis(hydroxymethyl)methyl]glycine, Dicine

Serinol (2.5 g, 26 mMol), chloroacetic acid (2.41 g, 26 mMol) and NaOH (3.2 ml 10N, 52 mMol) were dissolved in 25 ml water and stirred at room temperature for 16 h. The solution was concentrated on a rotoevaporator, and the resulting glass was redissolved in methanol. Addition of acetone gave a white solid (2 g, 51%) which was recrystallised from methanol/ethyl acetate. Mass spec calculated for C$_5$H$_{11}$NO$_4$: 149; found: 150 (M+1); $^1$H NMR in D$_2$O (0.75% TMS): 3.85 (m, 4H), 3.80 (s, 2H), 3.45 (m, 1H).

EXAMPLE 6

Synthesis of N-hydroxyethyl-glycine, Monocine 1.0 g of glyoxylic acid (10.85 mmol), 0.83 ml of ethanolamine (13.85 mmol), and 0.34 g of sodium cyanoborohydride (5 mmol) were stirred in methanol at room temperature for 48 hours. 1.0 ml of 12N HCl (10.85 mmol) was slowly added to the solution, which was then concentrated on a rotoevaporator. Addition of absolute ethanol with rapid stirring gave a white solid which was collected on a frit and dried in vacuo. FAB Mass spec calculated for $C_4H_9NO_3$: 119; found: 142 (m+Na), 164 (m+2Na); $^1$H NMR in $D_2O$: 3.85 (t, 5, 2H), 3.67 (s, 2H), 3.23 (t, 5, 2H).

EXAMPLE 7

Synthesis of N-[tris(hydroxymethyl)methyl]alanine, Methyltricine 2.5 g of 2-bromopropionic acid (16.4 mmol) and 1.6 ml of 10N NaOH (16.4 mmol) were dissolved in 25 ml of water and 1.98 g of N-[tris(hydroxymethyl)methyl]amine (16.4 mmol) were added with stirring. The solution was stirred at 80° C. for 6 hours during which 16 ml of 1N NaOH were added dropwise. The solvent was removed by rotoevaporation and the resulting glass was dried overnight in vacuo. Mass spec calculated for $C_7H_{15}NO_5$: 193; found: 194 (m+1), 216 (m+Na); $^1$H NMR in $D_2O$:3.66 (q, 7, 1H), 3.21 (s, 6H), 1.13 (d, 7, 3H).

EXAMPLE 8

Synthesis of N-[tris(hydroxymethyl)methyl]-β-alanine (β-Methyltricine)

1.0 g of Tris (8.26 mMol) and 1.0 ml of acrylonitrile (16 mMol) were stirred in methanol at 70° C. for 48 hours. The solvent was removed on a roloevaporator and absolute ethanol was added to the resulting glass. The unreacted Tris which precipitated from solution was filtered and the mother liquor was filtered through a short plug of silica gel. Concentration of the solution gave a white crystalline solid A (0.86 g, 60%). $^1$H NMR; 3.58 (s, 6H), 2.96 (t, 7, 2H), 2.65 (t, 7, 2H).

0.25 G of A (14 mMol) was refluxed in concentrated HCl for 16 hours. The solvent was stripped on a rotoevaporator and the resulting residue was dried overnight under vacuum at 80° C. The solution was evaporated on a rotoevaporator to give an off-white solid, N-[tris-(hydroxymethyl)methyl]-β-alanine ammonium chloride.

EXAMPLE 9

Preparation of Tc-L Precursor Solution

An aqueous precursor solution of ligand L, e.g. tricine, at 72 mg/ml concentration was prepared in deoxygenated, metal-free water. The precursor stock solution was adjusted to pH 7.1 with 1N NaOH solution. A second stock solution of $SnCl_2$—$2H_2O$, 10 mg/ml in 0.1N HCl, was prepared and added to the precursor stock solution to make it 100 ug/ml in $SnCl_2$—$2H_2O$. The precursor/$SnCl_2$ solution was mixed in equal proportions with $^{99m}TcO_4^-$ (30 mCi/ml). After a few minutes at room temperature, analysis for the formation of the Tc-ligand precursor complex was performed on ITLC-SG chromatography plates. Using an 8×1 cm plate, a 2.5 uL sample of the Tc-precursor solution is spotted at 1 cm and eluted with saline to yield Tc-colloid at the origin and Tc-precursor complex at the colvent front. Using a 10×1 cm plate, a 2.5 uL sample of the Tc-precursor solution is spotted at 1 cm and eluted with methylethylketone or 2:1 acetone:dichloromethane solution to yield Tc-precursor at the origin and $^{99m}TcO_4^-$ at the solvent front.

Results presented in Table 1 as % yield of technetium species in solution clearly demonstrate that this method is general to technetium complexes of ligands L exemplified in Examples 1, 5, 6 and 7. Functional substitutions on the tris(hydroxymethyl)methyl group or the glycine still yield quantitative formation of the Tc-precursor complex within minutes at room temperature. These solutions are suitable for protein labelling with no further modification.

EXAMPLE 10

Radiolabeling of IgG modified with SHNH with Tc-L precursors

The efficacy of radiolabelling IgG modified with SHNH (hydrazino-nicotinamide groups, as described in EPA 0384769) was measured with respect to Tc-precursor complexes as generated in Example 9 above. 100 uL of the respective Tc-precursor at 15 mCi/ml was mixed with an equal volume of IgG-SHNH, 4.9 mg/ml in 20 mM citrate 100 mM NaCl buffer pH 5.2, and incubated for one hour at room temperature. The solution was sampled at 60 minutes and analysed by thin layer chromatography using ITLC-SG plates, 1×8 cm, and saline eluant. Tc-labelled IgG-SHNH adheres to the origin of the plate and Tc-precursors as well as $^{99m}TcO_4^-$ elute to the solvent front.

The results, presented in Table 1 as % yield of Tc-IgG-SHNH (and corrected for Tc-colloid), clearly demonstrate that Tc-precursors formulated from polyhydroxy analogues of ligand L quantitatively radiolabel IgG-SHNH. Additionally, alkyl modification of glycine in ligand L to alanine, as exemplified in methyltricine, still yields quantitative radiolabelling of IgG-SHNH although the efficiency is decreased at room temperature. Therefore, the general use of polyhydroxy amino acid analogues of ligand L for the formation of Tc-precursor complexes and subsequent radiolabelling of proteins modified with SHNH is demonstrated.

TABLE 1

| Formation of Tc-precursor Complexes and Radiolabelling of IgG-SHNH | | | | |
|---|---|---|---|---|
| | % Yield of Technetium Species in Solution | | | % Yield of Tc-IgG-SHNH |
| Sample | TC-precursor | Tc-colloid | $TCO_4^-$ | 12.5 mCi/mg |
| Tc-Tricine | 98.5 | 0.2 | 1.3 | 97.4 |
| Tc-Methyltricine | 94.9 | 0.8 | 4.3 | 90.1 |
| Tc-Dicine | 99.3 | 0.1 | 0.6 | 98.9 |
| Tc-Monocine | 84.1 | 13.9 | 2 | 73.3 |
| Tc-β-Methyltricine | 57.6 | 18.2 | 24.2 | 75.4* |

*>60 min

We claim:

1. An intermediate complex for combination with antibody or antibody fragment components to produce an imaging agent, comprising $^{99m}$Tc complexed with the ligand L, $$(R^3)(R^4)(R^5)C\text{—}N(R)\text{—}C(R^1)(R^2)\text{—}(CH_2)_n\text{—}COOH \qquad L$$

where

R is hydrogen, hydroxyl, alkyl or hydroxyalkyl or

R and $R^1$ together form a mono-, di-, tri-, or tetra-methylene radical, or

R and $R^3$ together form a mono-, di-, tri-, or tetra-methylene radical, and $R^1$ and $R^2$ are the same or different and are selected from hydrogen, hydroxyl, alkyl, hydroxyalkyl, carboxyl, alkylcarboxyl, alkylamine, alkylthiol, aryl or $R^1$ and $R^2$ together form a tetra- or pentamethylene radical, and $R^3$ and $R^4$ and $R^5$ are the same or different and are selected from hydrogen, hydroxyl, alkyl, hydroxyalkyl, carboxyl, alkylcarboxyl, provided that at least two of $R^3$, $R^4$ and $R^5$ are hydroxylalkyl, and n is equal to 0, 1 or 2.

2. A complex as claimed in claim 1, wherein in the ligand, at least one of R, $R^1$ and $R^2$ is hydrogen.

3. A complex as claimed in claim 2, wherein in the ligand, at least two of R, $R^1$ and $R^2$ are hydrogen.

4. A complex as claimed in claim 1, wherein in the ligand, at least one of $R^3$, $R^4$ and $R^5$ is hydroxymethyl.

5. A complex as claimed in claim 1, wherein the ligand L is tricine.

6. A complex as claimed in claim 1, wherein the ligand L is dicine.

7. A complex as claimed in claim 1, wherein the ligand L is methyltricine.

8. A complex as claimed in claim 1, wherein the ligand L is β-methyltricine.

9. A method of forming the complex of claim 1, comprising the reduction of the pertechnetate ion in the presence of a ligand of general formula L.

* * * * *